United States Patent [19]

Janchitraponvej et al.

[11] Patent Number: 5,221,530

[45] Date of Patent: Jun. 22, 1993

[54] MILD CONDITIONING SHAMPOO WITH A HIGH FOAM LEVEL CONTAINING AN ANIONIC SURFACTANT-CATIONIC ACRYLATE/ACRYLAMIDE COPOLYMER CONDITIONING AGENT

[75] Inventors: Ben Janchitraponvej, Niles; William J. Brown, Flossmoor, both of Ill.

[73] Assignee: Helene Curtis, Inc., Chicago, Ill.

[21] Appl. No.: 719,818

[22] Filed: Jun. 24, 1991

[51] Int. Cl.$^5$ ............................................... A61K 7/075
[52] U.S. Cl. ............................ 424/70; 252/DIG. 13; 424/47; 424/71; 424/78.08; 424/78.17; 424/78.18
[58] Field of Search ............ 424/70, 47, 78, 81, 424/71, 78.08, 78.17, 78.18; 252/DIG. 13

[56] References Cited

U.S. PATENT DOCUMENTS

| | | | |
|---|---|---|---|
| 4,140,759 | 2/1979 | Mausner | 424/70 |
| 4,402,977 | 9/1983 | Grollier et al. | 424/70 |
| 4,591,610 | 5/1986 | Grollier | 424/70 X |
| 4,657,690 | 4/1987 | Grollier et al. | 424/70 X |
| 4,842,851 | 6/1989 | Grollier et al. | 424/70 |
| 4,983,383 | 1/1991 | Maksimoski et al. | 424/70 |
| 5,034,218 | 7/1991 | Duvel | 424/70 |
| 5,037,818 | 8/1991 | Sime | 514/183 |
| 5,085,857 | 2/1992 | Reid et al. | 424/70 |
| 5,100,660 | 3/1992 | Hawe et al. | 424/78.35 |

FOREIGN PATENT DOCUMENTS 0093601 11/1983 European Pat. Off. .
2-59510 2/1990 Japan .

*Primary Examiner*—Thurman K. Page
*Assistant Examiner*—Robert H. Harrison
*Attorney, Agent, or Firm*—Marshall, O'Toole, Gerstein, Murray & Bicknell

[57] ABSTRACT

A conditioning shampoo containing an anionic surfactant, in an amount of about 5% to about 25% by weight, and a cationic acrylate/acrylamide copolymer conditioning agent material, in an amount of about 0.1% to about 20% by weight, has extended product stability, excellent overall conditioning to human hair, particularly superior wet and dry combing properties, and unexpectedly maintains very high levels of foam, with a mild anionic cleansing detergent, e.g., an anionic carboxylate detergent, or with lower amounts of a strong anionic cleansing detergent, such as a long chain ($C_{12}$–$C_{22}$) alkyl sulfate, and/or a long chain ($C_{12}$–$C_{22}$) partially or fully ethoxylated alkyl sulfate; and/or a long chain ($C_{12}$–$C_{22}$) sulfonate.

22 Claims, No Drawings

MILD CONDITIONING SHAMPOO WITH A HIGH FOAM LEVEL CONTAINING AN ANIONIC SURFACTANT-CATIONIC ACRYLATE/ACRYLAMIDE COPOLYMER CONDITIONING AGENT

FIELD OF THE INVENTION

The present invention is directed to a hair conditioning shampoo composition and to a method of treating hair with the composition to provide the hair with improved wet stage and dry stage conditioning properties as well as other conditioning properties, such as softness, without residual build-up of conditioning agents on the hair and, at the same time, thoroughly cleansing the hair with a cleansing detergent that develops an unexpectedly high foam level in combination with the copolymer conditioning agent. More particularly, the present invention is directed to a hair conditioning shampoo composition including one or more anionic cleansing surfactants, such as ammonium lauryl sulfate, and/or a mild carboxylate surfactant together with a cross-linked copolymer of a quaternary amino functional acrylate and acrylamide conditioning agent, such as SALCARE SC92 of ALLIED COLLOIDS of Suffolk, Va. Surprisingly, the composition develops copious amounts of foam for a conditioning shampoo while achieving excellent conditioning benefits, even in the absence of a strong anionic cleansing detergent, such as a long chain alkyl sulfate, or containing a small quantity (less than about 9% by weight) of a fully or partially ethoxylated long chain alkyl sulfate or sulfonate. Further, the anionic surfactant/cationic conditioning agent components are compatible and stable while developing surprisingly high amounts of foam without the problem of anionic surfactant-cationic conditioning agent incompatibility.

BACKGROUND OF THE INVENTION

Soiled human hair is shampooed to remove sebum that is naturally secreted by the head as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum, are those that contain high lather synthetic anionic detergents, such as the long chain alkyl sulfates, the partially ethoxylated long chain alkyl sulfates and the long chain sulfonates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb, in either the wet or dry state because the individual hair fibers tend to snarl, kink, and interlock with each other. Particularly, prior to complete drying of thoroughly cleansed hair, in this after-shampoo stage, the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away", thereby further reducing the combing or brushing property of the hair. Generally, these above-outlined problems that result from synthetic detergent cleansing of the hair, particularly in the high-lather synthetic anionic detergents, have been eleviated either by the after-shampoo treatment of the hair with hair conditioners, for example, in the form of a hair rinse, or by including hair conditioners directly within the shampoo composition.

After-shampoo hair conditioning compositions are easily formulated but are inconvenient to use because of the necessity of applying the conditioner to the hair in a separate stage, after shampooing. The prepartion of a conditioning shampoo has been more difficult because of inherent incompatibility problems between anionic surfactants and the cationic compounds that are good conditioning agents. Contact between an anionic surfactant and a cationic surfactant or cationic polymer produces a precipitate that forms immediately or causes an interaction between the anionic and cationic compounds that significantly reduces their respective cleaning and conditioning properties, and especially a very noticeable severe loss of foam attributed by the anionic cleansing surfactant. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, Jun. 22, 1976 to Drakoff; U.S. Pat. No. 4,364,837, Dec. 21, 1982 to Pader; British Patent No. 849,433, Sep. 28, 1960 to Woolston; U.S.. Pat. No. 4,741,855 to Grote, et al.; U.S. Pat. Nos. 4,788,006 and 4,902,499 to Bolich, Jr. et al. and U.S. Pat. No. 4,704,272 to Oh et al. The silicones are well known to substantially reduce the foaming of anionic cleansing surfactants.

A particularly difficult problem to solve in silicone-containing conditioning shampoos is that of providing a conditioning shampoo that provides excellent cleansing of the hair while providing high foaming and, at the same time, also has excellent conditioning performance. The capability of providing excellent conditioning, cleansing and foam levels is achieved with the compositions of the present invention. In accordance with one embodiment of the present invention, a complete breakthrough in the art is achieved in a composition that not only achieves excellent conditioning properties while retaining excellent cleansing and foam levels in a stable conditioning shampoo, but all of these properties are achieved in a mild shampoo that is gentle to the hands without including a long chain alkyl sulfate or sulfonate, or without the typically high levels, e.g., 10%+, of a long chain fully or partially ethoxylated alkyl sulfate cleansing detergent. Optionally, a number of materials can be included in the conditioning shampoos of the present invention for purposes of thickening and stabilization such as xanthan gum, long chain acyl derivatives, long chain amide or amine oxides, and long chain alkanolamides, as disclosed in U.S. Pat. Nos. 4,788,006; 4,704,272; and 4,741,855, hereby incorporated by reference.

SUMMARY OF THE INVENTION

In accordance with the principles of the present invention, it has been found, surprisingly, that a conditioning shampoo containing a cleansing surfactant, in an amount of about 5% to about 25% by weight, and a cross-linked cationic acrylate/acrylamide copolymer conditioning agent material, in an amount of about 0.1% to about 20% by weight, has extended product stability, excellent overall conditioning to human hair, particularly superior wet and dry combing properties, and unexpectedly maintains very high levels of foam, with predominantly a mild anionic cleansing detergent, e.g., an anionic carboxylate detergent, or with lower amounts of a strong anionic cleansing detergent, e.g., about 3% to less than about 9% by weight of a long chain ($C_{12}$–$C_{22}$) alkyl sulfate, and/or a long chain ($C_{12}$–$C_{22}$) partially or fully ethoxylated alkyl sulfate, and/or a long chain ($C_{12}$–$C_{22}$) alkyl sulfonate. Preferably, the total amount of anionic surfactants in the compositions of the present invention is in the range of about 15% to about 20% by weight of the composition, and the preferred amount of cross-linked acrylate/acrylamide conditioning agent is in the range of about 0.5% to about 8% by weight.

The compositions of the present invention are stable and do not exhibit the inherent anionic surfactant/cationic conditioning agent incompatibility while providing excellent cleansing, conditioning and foam levels in a surprisingly mild conditioning shampoo. It was further surprisingly and unexpectedly found that hair treated with the compositions of the present invention is thoroughly cleansed at high foam levels and exhibits improved physical and cosmetic properties, such as gloss, thickness, manageability, softness and body without irritation to the hands even after multiple uses, such as by a beauty parlor shampoo person.

Therefore, an aspect of the present invention is to provide a hair-treating composition that cleanses the hair and imparts improved physical properties and cosmetic properties to the hair in a single application from a mild conditioning shampoo that developes unexpectedly high foam quantities and/or is unexpectedly mild.

Another aspect of the present invention is to provide a physically stable conditioning shampoo containing an anionic surfactant, and a cationic acrylate/acrylamide copolymer conditioning agent, that is mild and develops excellent foam levels.

Another aspect of the present invention is to provide a new and improved conditioning shampoo containing a strong anionic detergent, such as a long chain alkyl sulfate, long chain alkyl ether sulfate, and/or long chain sulfonate, in an amount less than about 9% by weight, preferably less than about 6% by weight, that is compatible with a cross-linked cationic acrylate/acrylamide copolymer conditioning agent, that maintains an unexpectedly high foam level at a loading of strong anionic detergent much lower than in prior art conditioning shampoos having an equivalent foam level.

Still another aspect of the present invention is to provide a new and improved conditioning shampoo including about 5% to about 25% of an anionic surfactant; and about 0.1% to about 20% of a cross-linked cationic acrylate/acrylamide copolymer conditioning agent and optionally an emulsion stabilizer and/or a viscosity increasing agent for aqueous emulsions, each in an amount of about 0 to about 10% by weight, active, preferably about 0.1% to about 5% by weight.

A further aspect of the present invention is to provide a new and improved method of cleansing and conditioning hair, simultaneously, with a composition containing one or more anionic surfactants that are mild due to their molecular structure or due to their presence in lower than normal amounts, together with a cationic acrylate/acrylamide copolymer conditioning agent, while providing high foam levels, excellent cleansing, and excellent conditioning in a mild conditioning shampoo.

The above and other aspects and advantages of the present invention will become apparent from the following detailed description of the preferred embodiments.

DETAILED DESCRIPTION OF THE PREFERRED EMBODIMENTS

The aqueous conditioning shampoo compositions of the present invention generally includes water; an anionic surfactant in an amount of about 6% to about 25% by weight of the compositions; and a cross-linked cationic acrylate/acrylamide copolymer conditioning agent in an amount of about 0.1% to about 20% by weight of the composition.

The conditioning shampoo of the present invention provides the hair with improved physical and cosmetic conditioning properties, such as gloss, thickness, softness, and manageability, including excellent wet and dry combing properties and body simultaneously with excellent cleansing at high foam levels in a mild conditioning shampoo. As will be demonstrated more fully hereinafter, it is surprising and unexpected that the composition of the present invention, including an anionic cleansing compound, and a cationic conditioning compound is able to provide the demonstrated cleansing at such a high foam level in a mild composition.

The anionic cleansing surfactant used in the composition and method of the present invention can be any of the anionic surfactants known or previously used in the art of hair shampoos. An anionic cleansing surfactant should be included in the composition of the present invention to effectiely cleanse the hair and generates a high, stable foam level that consumers equate with cleaning efficiency. While nonionic and amphoteric surfactants have not been as effective in cleansing the hair and do not provide the high foam level desired by consumers, surprisingly, it has been found that the composition of the present invention provides excellent foam levels with the less strong anionic cleansing detergents or with the strong anionic detergents at levels generally below about 9% by weight of the composition, particularly when the foam level is boosted with one or more common foam boosters, such as a betaine or other foam booster. Optionally, nonionic, amphoteric and/or zwitterionic surfactants can be included in the compositions of the present invention in addition to one or more anionic surfactants, to help stabilize foam, to provide a suitable viscosity, or to give other functional or esthetic properties to the composition.

Usually, the anionic cleansing surfactant includes a hydrophobic moiety, such as a carbon chain including from about eight carbon atoms to about 30 carbon atoms, and particularly from about 12 carbon atoms to about 22 carbon atoms and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether surfates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof. Many addition cleansing surfactants are described in McCUTCHEON'S DETERGENTS AND EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium, alkylammonium or hydroxyalkylammonium salt, wherein the alkyl moiety includes from one to about three carbon atoms. The alkyl sulfates and alkyl ether sulfates are particularly effective classes of anionic cleansing surfactants and can be incorporated into the compositions of the present invention in lower amounts than necessary to achieve sufficient foam levels in prior art conditioning shampoos. Alternatively, the weaker and milder anionic cleansing detergents can be incorporated in amounts commonly needed for the stronger anionic cleansing detergents while achieving equivalent foam levels and cleansing.

Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. Also useful are the zwitterionic betaines, e.g., cocamdopropyl betaine, cocamidopropyl hydroxysultaine, and the like; and the anionic carboxylate cleansing detergents, such as C11-15 Pareth-7 carboxylic acid, C11-15 Pareth-9, C11-15 Pareth-12, C11-15 Pareth-20, C11-15 Pareth-30, C11-15 Pareth-40, C11-21 Pareth-10, C12-13 Pareth-5 carboxylic acid, C12-15 Pareth-2 phosphate, C12-15 Pareth-7 carboxylic acid, C12-15 Pareth-9, C12-15 Pareth-12, C14-15 Pareth-13, C22-24 Pareth-33, cocaminobutyric acid, cocaminopropionic acid, coceth-7 carboxylic acid, cocoamphodipropionic acid, coconut acid, deceth-7 carboxylic acid, hydrogenated coconut acid, hydrogenated menhaden acid, hydrogenated tallow acid, hydroxystearic acid, isostearic acid, lanolin acid, lauraminopropionic acid, laureth-5 carboxylic acid, laureth-10 carboxylic acid, lauroamphodipropionic acid, linoleic acid, linolenic acid, linseed acid, MEA-laureth-6 carboxylate, myristaminopropionic acid, palmitic acid, sodium C12-15 Pareth-6 carboxylate, sodium C12-15 Pareth-7 carboxylate, sodium ceteth-13 carboxylate, sodium isosteareth-6 carboxylate, sodium isosteareth-11 carboxylate, sodium laureth-13 carboxylate, sodium trideceth-7 carboxylate, sodium trideceth-12 carboxylate, trideceth-4 carboxylic acid, trideceth-7 carboxylic acid, trideceth-15 carboxylic acid, and trideceth-19 carboxylic acid.

The following low-irritation surfactants are particuarly useful in formulating a "baby" shampoo having high performance in terms of foam level and cleansing while achieving exceptional mildness:

ANIONICS:
Disodium Laureth Sulfosuccinate;
Disodium Lauroamido MEA Sulfosuccinate;
Disodium Ricinoleamido MEA Sulfosuccinate;
Ceteareth-25-Carboxylic Acid;
Trideceth-7-Carboxylic Acid;
Pareth-25-6-Carboxylic Acid;
Trideceth-4-Carboxylic Acid;
Trideceth-19-Carboxylic Acid;
Sodium Trideceth-12-Carboxylate;
Sodium Ceteth-13-Carboxylate;
Laureth-5-Carboxylic Acid (SANDOPAN® LA 8)
Sodium Oleth-13-Carboxylate;
Sodium Ceteareth-5-Carboxylate;
Sodium Ceteareth-9-Carboxylate;
Isosteareth-6-Carboxylic Acid; and
Isosteareth-11-Carboxylic Acid.

NONIONICS:
PEG 30 Glyceryl Mono Cocoate;
PEG 78 Glyceryl Mono Cocoate;
PEG 82 Glyceryl Mono Tallowate;
PEG 200 Glyceryl Mono Tallowate; and
PEG 20 Glyceryl Mono Tallowate.

AMPHOTERICS:
Cocampho-Carboxyglycinate (VARION® 2C)
Lauroampho-Carboxyglycinate (VARION® 2L)
Cocamidopropyl Betaine; and
Cocamidopropyl Hydroxysultaine (VARION® CAS).

The emulsified conditioning shampoo of the present invention also includes a cationic acrylate/acrylamide copolymer conditioning agent such as SALCARE SC92 of Allied Colloids (POLYQUATERNIUM 32). The cationic conditioning agent used in the emulsified conditioning composition and method of the present invention is an oil-soluble, water-dispersible cross-linked, acrylate/acrylamide copolymer, quaternized with methyl chloride, wherein the acrylate monomers have an amino functionality (e.g., dimethylaminoethyl methacrylate). Generally, the copolymer has a weight average molecular weight in the range of about 10,000 to about 5 million.

To achieve the full advantage of the present invention, a foam booster, in an amount of about 0.1% to about 20% by weight of the composition, is included in the composition to aid in the formation of copious amount of foam. Suitable foam boosters include one or more of the following:

Capramide DEA
Cetearyl Alcohol

Cetyl Alcohol
Cetyl Betaine
Cocamide
Cocamide DEA
Cocamide MEA
Cocamide MIPA
Cocamidoethyl Betaine
Cocamidopropylamine Oxide
Cocamidopropyl Betaine
Cocamidopropyl Hydroxysultaine
Cocamine Oxide
Cocoamphodipropionic Acid
Coco-Betaine
Coco-Morpholine Oxide
Coconut Alcohol
Coco/Oleamidopropyl Betaine
Coco-Sultaine
Cocoyl Hydroxyethyl Imidazoline
Cocoyl Sarcosinamide DEA
DEA-Cocoamphodipropionate
DEA-Lauraminopropionate
Decylamine Oxide
Decyl Betaine
Dihydroxyethyl C8-10 Alkoxypropylamine Oxide
Dihydroxyethyl C9-11 Alkoxypropylamine Oxide
Dihydroxyethyl C12-15 Alkoxypropylamine Oxide
Dihydroxyethyl Cocamine Oxide
Dihydroxyethyl Stearamine Oxide
Dihydroxyethyl Tallowamine Oxide
Disodium Isostearyl Sulfosuccinate
Hydrogenated Tallow Amine Oxide
Hydroxyethyl Hydroxypropyl C12-15 Alkoxypropylamine Oxide
Hydroxyethyl Stearamide-MIPA
Isopropyl Stearate
Isostearamidopropylamine Oxide
Isostearamidopropyl Morpholine Oxide
Lauramide
Lauramide DEA
Lauramide MEA
Lauramide MIPA
Lauramidopropylamine Oxide
Lauramidopropyl Betaine
Lauramine Oxide
Lauryl Alcohol
Lauryl Betaine
Lauryl Sultaine
Myristamide DEA
Myristamide MEA
Myristamide MIPA
Myristamidopropylamine Oxide
Myristamidopropyl Betaine
Myristamine Oxide
Myristaminopropionic Acid
Myristyl Alcohol
Myristyl Betaine
Oleamidopropylamine Oxide
Oleamidopropyl Betaine
Oleamidopropyl Hydroxysultaine
Oleamine Oxide
Oleyl Betaine
Palmamide DEA
Palmamide MEA
Palmamide MIPA
Palmamidopropyl Betaine
Palmitamide DEA
Palmitamide MEA
Palmitamidopropylamine Oxide
Palmitamidopropyl Betaine
Palmitamine Oxide
Palm Kernel Alcohol
Palm Kernelamide DEA
Palm Kernelamide MEA
Palm Kernelamide MIPA
Peanutamide MEA
Peanutamide MIPA
PEG-6 Cocamide
PEG-3 Lauramide
PEG-5 Lauramide
PEG-6 Lauramide
PEG-3 Lauramine Oxide
Sodium Cocoamphoacetate
Sodium Cocoamphopropionate
Sodium Lauraminopropionate
Sodium Lauroamphopropionate
Sodium Lauroyl Sarcosinate
Sodium Myristoamphoacetate
Sodium Myristoyl Sarcosinate
Stearyl Alcohol
TEA-Hydrogenated Tallow Glutamate
TEA-Lauraminopropionate
TEA-Myristaminopropionate
Undecylenamide DEA
Undecylenamide MEA
Undecylenamidopropylamine Oxide One or more zwitterionic detergents, such as a betaine, in an amount of about 5% to about 25% by weight of the composition aids in stabilizing the composition but generally is not necessary to achieve a stable composition. Suitable betaines include, for example:

Betaine
Cetyl Betaine
Cocamidoethyl Betaine
Cocamidopropyl Betaine
Cocamidopropyl Hydroxysultaine
Coco-Betaine
Coco/Oleamidopropyl Betaine
Coco-Sultaine
Decyl Betaine
Hydrogenated Tallow Betaine
Isostearamidopropyl Betaine
Lauramidopropyl Betaine
Lauryl Betaine
Lauryl Sultaine
Myristamidopropyl Betaine
Myristyl Betaine
Oleamidopropyl Betaine
Oleamidopropyl Hydroxysultaine
Oleyl Betaine
Palmamidopropyl Betaine
Palmitamidopropyl Betaine
Ricinoleamidopropyl Betaine
Stearamidopropyl Betaine
Stearyl Betaine
Tallowamidopropyl Betaine
Tallowamidopropyl Hydroxysultaine
Wheat Germamidopropyl Betaine Other compounds useful for composition stabilization, in an amount of about 0.1% to about 10% by weight of the composition include any one or more of the following:

Acetylated Glycol Stearate
Aluminum Caprylate
Aluminum Dilinoleate
Aluminum Distearate
Aluminum Isostearates/Laurates/Palmitates
Aluminum Isostearates/Laurates/Stearates
Aluminum Isostearates/Myristates
Aluminum Isostearates/Palmitates
Aluminum Isostearates/Stearates
Aluminum Lanolate
Aluminum Myristates/Palmitates
Aluminum Stearate
Aluminum Stearates
Aluminum Tristearate
Beeswax
Bentonite
C9-11 Alcohols
C12-13 Alcohols
C12-15 Alcohols
C12-16 Alcohols -continued C14-15 Alcohols
C15-18 Glycol
Calcium Carrageenan
Calcium Stearate
Carbomer 910
Carbomer 934
Carbomer 934P
Carbomer 940
Carbomer 941
Carboxymethyl Hydroxyethylcellulose
Carboxymethyl Hydroxypropyl Guar
Carrageenan
Cellulose Gum
Ceresin
Ceteraryl Alcohol
Cetyl Alcohol
Cholesterol
Coconut Alcohol
Ethylene/Acrylate Copolymer
Ethylene/Vinyl Acetate Copolymer
Guar Gum
Hydroxybutyl Methylcellulose
Hydroxyethylcellulose
Hydroxyethyl Ethylcellulose
Hydroxypropylcellulose
Hydroxypropyl Guar
Hydroxypropyl Methylcellulose
Isopropyl Ester of PVM/MA Copolymer
Karaya Gum
Lanolin
Lanolin Alcohol
Lauryl Alcohol
Locust Bean Gum
Maltodextrin
Methoxy PEG-22/Dodecyl Glycol Copolymer
Methylcellulose
Microcrystalline Cellulose
Microcrystalline Wax
Montmorillonite
Myristyl Alcohol
Ozokerite
Pectin
PEG-2M
PEG-5M
PEG-7M
PEG-9M
PEG-14M
PEG-20M
PEG-23M
PEG-45M
PEG-90M
PEG-115M
PEG-22/Dodecyl Glycol Copolymer
PEG-45/Dodecyl Glycol Copolymer
Polyacrylic Acid
Polyethylene
Polyvinyl Acetate
Potassium Alginate
Potassium Carrageenan
PVM/MA Copolymer
PVP/VA Copolymer
Saccharated Lime
Sodium Acrylate/Vinyl Alcohol Copolymer
Sodium C4-12 Olefin/Maleic Acid Copolymer
Sodium Carboxymethyl Dextran
Sodium Carrageenan
Sodium Cellulose Sulfate
Sodium Polymethacrylate
Sodium Polynaphthalene Sulfonate
Sodium Polystyrene Sulfonate
Stearyl Alcohol
Stearylvinyl Ether/Maleic Anhydride Copolymer
Styrene/Maleic Anhydride Copolymer
Synthetic Beeswax
Synthetic Wax
Tallow Alcohol
Tragacanth Gum
Tridecyl Alcohol
Xanthan Gum Other common cosmetic components and additives that can be incorporated into the conditioning shampoos of the present invention, as long as the basic properties of conditioning, cleansing and high foam levels are not adversely affected include, for example, fragrances, dyes, hair colorants, opacifiers, pearlescing agents, dandruff control agents, hydrotropes, foam stabilizers, solubilizers, preservatives, water softening agents, acids, bases, buffers and the like. These optional components and additives usually will be present in weight percentages of less than about 2% each, and from about 5% to about 10% by weight in total. The vehicle of the hair-treating composition is generally predominantly water, but organic solvents also can be used in order to help solubilize compounds that are not sufficiently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether; and mixtures thereof. These non-aqueous solents can be present in the hair-treating composition of the present invention in an amount from about 1% to 100% by weight and, in particular, from about 5% to about 50% by weight, relative to the total weight of the carrier vehicle in the composition.

The conditioning shampoos of the present invention also can be thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount ranging from about 0.1% to about 5%, and preferably from about 0.25% to about 1%, by weight relative to the total weight of the composition.

If instability of the composition is a problem, the composition also can include a suspending agent for the conditioning agent or other water-insoluble material, in an amount of about 0.5% to about 10%, by total weight of the composition. The particular suspending agent is not critical and can be selected from any materials known to suspend water-insoluble liquids or solids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in literature, such as McCUTCHEON'S DETERGENTS AND EMULSIFIERS, 1989 Annual, published by McCutcheon Division, MC Publishing Co.

The conditioning shampoos also can include other emulsifiers, inorganic salts, humectants and similar materials to provide esthetic properties and desirable physical properties to the composition. Generally, such optional ingredients are present in weight percentages ranging from about 0.1% to about 10% each, and from about 0.1% to about 20% in total, relative to the total weight of the composition.

For example, representative nonionic surfactants that can be included in the hair-treating composition of the present invention include esters of polyols and sugars;

the polyethoxylated and/or polypropoxylated alkylphenols; and the condensation products of ethylene oxide with long chain amides. All these nonionic surfactants, as well as numerous others not cited here, are well known in the art and are fully described in the literature.

The compositions of the present invention can be relatively viscous dispersions that are stable to phase separation at a temperture of about 20° C. to about 25° C. for a period of time of at least 24 hours after preparation, and typically are stable to phase separation indefinitely at such temperatures. The compositions of the present invention usually are emulsions that are stable to phase separation at a temperature of about 25° C. for a period of about 24 hours after preparation. The emulsions should demonstrate sufficient stability to phase separation at temperatures normally found in commercial product storage and shipping to remain unaffected for period of one year or more.

The following examples illustrate various conditioning shampoos made in accordance with the present invention:

EXAMPLE 1

| | | WT. % |
|---|---|---|
| 1. | Water | 59.15 |
| 2. | Acrylate/acrylamide copolymer Allied Colloid D.P. 64297C (50% in mineral oil) | 2.50 |
| 3. | SURFODONE ® QSP (polylauryl pyrrolidone) polymeric emulsion stablizer | 0.50 |
| 4. | SANDOPAN ® LA 8 (carboxylate surfactant) | 7.00 |
| 5. | SURFINE ® WNT A (carboxylate surfactant) | 7.00 |
| 6. | KOH (50%) | 0.60 |
| 7. | Cocamidopropyl Hydroxysultaine (40%) (VARION ® CAS) | 15.00 |
| 8. | C$_{16-18}$ amine oxide (40%) (SCHERCAMOX ® CMA) | 2.00 |
| 9. | GLUCAMATE ® DOE 120* (thickener) | 0.50 |
| 10. | Color, fragrance, preservative pH = 5.19 Viscosity (25° C.) = 3,000 cps. | q.s. |

*polyethylene glycol diester of methyl glucose and oleic acid with an average of 120 moles of ethylene oxide.

EXAMPLE 2

| | | WT. % |
|---|---|---|
| 1. | Water | 20.00 |
| 2. | Acrylate/acrylamide copolymer Allied Colloid D.P. 64297C (50% in mineral oil) | 2.00 |
| 3. | Cocamidopropyl Hydroxysultaine (40%) (VARION ® CAS) | 15.00 |
| 4. | Cocamide DEA (foam booster) | 4.00 |
| 5. | SANDOPAN ® LA 8 (carboxylate surfactant) | 15.00 |
| 6. | Water | 42.05 |
| 7. | KOH (50%) | 1.40 |
| 8. | Perfume | 0.30 |
| 9. | Glydant | 0.20 |
| 10. | Kathon CG pH = 5.0 Viscosity (25° C.) = 2,000 cps. | 0.05 |

Procedure Example 2:

Add the sultaine (#3) and the acrylate/acrylamide copolymer (#2) to water (#1) with mixing (1 hour). Then add the Cocamide DEA (#4) and mix until homogeneous (lump free). Into a separate container, add the SANDOPAN ® carboxylate surfactant (#5) to water (#6) followed by the KOH (#7) addition and then mix all items #1 through #7. The perfume (#8), glydant (#9) and Kathon CG (#10) then are added.

EXAMPLE 3

| | | WT. % |
|---|---|---|
| 1. | Water | 36.00 |
| 2. | SURFADONE ® QSP (polylauryl pyrrolidone) polymeric emulsion stabilizer | 0.60 |
| 3. | Acrylate/Acrylamide Copolymer Allied Colloid D.P. 65780E (50% mineral oil) | 3.00 |
| 4. | Surfactant Blend: | 20.00 |
| | (a) ALES (1 mole ethoxylation) (4.5%) | |
| | (b) lauramide DEA (2.5%) | |
| | (c) ammonium xylene sulfonate (0.6%) | |
| | (d) water q.s. | |
| 5. | KOH (50%) | 0.50 |
| 6. | SANDOPAN ® LA 8 (carboxylate surfactant) | 15.00 |
| 7. | KOH | 1.00 |
| 8. | Cocamidopropyl Hydroxysultaine (40%) (VARION ® CAS) | 10.00 |
| 9. | Perfume | 0.50 |
| 10. | Glydant | 0.20 |
| 11. | Kathon CG | 0.05 |
| 12. | Cold pearl mix | 3.00 |
| 13. | Cocamide DEA FO (foam booster) | 3.00 |
| 14. | Water, color | 7.15 |

Procedure Example 3:

Add (#2) in (#1), mix until no lumps, then add (#3) and mix until a soft gel is formed in about 40 minutes, avoid aeration;

Add (#4), mix for 5 minutes (precipitation is observed);

Add (#5) and (#6) and mix for 5 minutes;

Add (#7), mix until product is uniform (pH 4.5);

Add (#8), gradually, add (#9), (#10), (#11), (#12), (#13) and (#14).

pH 4.5

ADD KOH (50%)-0.6% to pH 5.13

FINAL pH-5.13 Viscosity (25° C.)-6,300 cps.

The composition of Example 3 is stable at 110° F. for at least 4 weeks, with temperature stability testing continuing.

To determine if the compositions of the present invention are compatible with a relatively low percentage of sodium lauryl ether (1 mole of ethoxylation) sulfate (SLES), Example 4 incorporates 5% by weight of SLES together with about 15% of other, mild carboxylate anionic surfactants.

EXAMPLE 4

| | | WT. % |
|---|---|---|
| 1. | Water, Soft | 22.72 |
| 2. | SURFODONE ® QSP (polylauryl pyrrolidone) polymeric emulsion stabilizer | 0.38 |
| 3. | Acrylate/Acrylamide Copolymer Allied Colloid D.P. 65780E (50% in mineral oil) | 1.90 |
| 4. | Water | 22.75 |
| 5. | SANDOPAN ® LA 8 (90%) (carboxylate surfactant) | 15.00 |

-continued

| | | WT. % |
|---|---|---|
| 6. | KOH (50%) | 1.50 |
| 7. | SLES (25%) | 20.00 |
| 8. | Cocamidopropyl Hydroxysultaine (40%) (VARION ® 2L) | 10.00 |
| 9. | Cocamide DEA (foam stabilizer) | 3.00 |
| 10. | Perfume | 0.50 |
| 11. | Kathon CG | 0.05 |
| 12. | Glydant | 0.20 |
| 13. | $C_{16-18}$ Amine Oxide (40%) SHERCOMOX ® CMA | 2.00 |
| | pH = 6.0 | |
| | Viscosity (25° C.) = 8,500 cps. | |

Procedure Example 4

Add (#2) to (#1), mix well and add (#3), mix until soft gel is formed.

Add remaining ingredients. Allow 5 minutes of mixing for each addition.

The composition of Example 4 remained stable for at least 14 days at 110° F.

EXAMPLE 5

The following formulation containing 17% by weight of a strong anionic surfactant, ammonium lauryl sulfate (ALS), was unstable within 10 minutes at 110° F.:

| | | WT. % |
|---|---|---|
| 1. | Water, Soft | 32.95 |
| 2. | Acrylate/Acrylamide Copolymer Allied Colloid SALCARE SC92 (50% in mineral oil) | 3.00 |
| 3. | Ammonium lauryl sulfate (30%) | 60.00 |
| 4. | Cocamide DEA (foam stabilizer) | 3.00 |
| 5. | Fragrance | 0.50 |
| 6. | Kathon CG | 0.05 |
| 7. | Glydant | 0.20 |
| 8. | Citric Acid | 0.30 |
| | pH = 5.8 | |
| | Viscosity (25° C.) = 2,000 cps. | |

EXAMPLE 6

Similarly to Example 5, the following formulation containing 17% by weight sodium lauryl sulfate (SLS) also was unstable within 10 minutes at 110° F.:

| | | WT. % |
|---|---|---|
| 1. | Water, Soft | 32.95 |
| 2. | Acrylate/Acrylamide Copolymer Allied Colloid SALCARE SC92 (50% in mineral oil) | 3.00 |
| 3. | Sodium lauryl sulfate (30%) | 60.00 |
| 4. | Cocamide DEA (foam stabilizer) | 3.00 |
| 5. | Fragrance | 0.50 |
| 6. | Kathon CG | 0.05 |
| 7. | Glydant | 0.20 |
| 8. | Citric Acid | 0.30 |
| | pH = 5.35 | |
| | Viscosity (25° C.) = 3,500 cps. | |

EXAMPLE 7

The following formulation shows the unexpected foam maintenance ability of the cationic cross-linked copolymers of a quaternary amino functional acrylate and acrylamide conditioning agent by substituting it with a typical silicone blend (33% SE 30 gum and 67% SF96-350 oil). The substitution resulted in instability of the composition, with the silicone floating on top of the composition; and very poor lather;

| | | WT. % |
|---|---|---|
| 1. | Water, Soft | 59.65 |
| 2. | SURFODONE ® QSP (polylauryl pyrrolidone) polymeric emulsion stabilizer | 0.50 |
| 3. | Silicone Blend 33% SE30 67% SF96-350 | 2.00 |
| 4. | SANDOPAN ® LA 8 (90%) (carboxylate surfactant) | 7.00 |
| 5. | SURFINE ® WNT A (Sodium Pareth 25-7 (carboxylate surfactant) | 7.00 |
| 6. | KOH (50%) | 0.60 |
| 7. | GLUCAMATE ® DOE 120 (thickener) | 0.50 |
| 8. | Cocamidopropyl Hydroxysultaine (40%) (VARION ® CAS) | 15.00 |
| 9. | Cocamide DEA (foam stabilizer) | 5.00 |
| 10. | $C_{16-18}$ Amine Oxide (40%) SCHERCOMOX ® CMA | 2.00 |
| 11. | Perfume | 0.50 |
| 12. | Glydant | 0.20 |
| 13. | Kathon CG | 0.05 |
| | pH = 5.5 | |
| | Viscosity (25° C.) = 3,000 cps. | |

RESULTS: Silicone floated on top. Product is unstable at room temperature, poor lather.

What is claimed is:

1. A mild conditioning shampoo capable of thoroughly cleansing and conditioning hair while maintaining a high foam level comprising water, an anionic surfactant in an amount of about 5% to about 25% by weight of the composition, and a cationic oil-soluble, water-dispersible cross-linked quaternary acrylate/acrylamide copolymer in an amount of about 0.1% to about 20% by weight of the composition.

2. The composition of claim 1, wherein the anionic surfactant is selected from the group consisting of disodium laureth sulfosuccinate; disodium lauroamide MEA sulfosuccinate; disodium ricinoleamido MEA sulfosuccinate; ceteareth-25-carboxylic acid salt; trideceth-7-carboxylic acid salt; pareth-25-6-carboxylic acid salt; trideceth-4-carboxylic acid salt; trideceth-19-carboxylic acid salt; sodium trideceth-12-carboxylate; sodium ceteth-13-carboxylate; laureth-5-carboxylic acid salt; sodium laureth-13-carboxylate; sodium oleth-13-carboxylate; sodium ceteareth-5-carboxylate; sodium ceteareth-9-carboxylate; isosteareth-6-carboxylic acid salt; and isosteareth-6-carboxylic acid salt; and isosteareth-11-carboxylic acid salt.

3. The composition of claim 1 further including a long chain ($C_{12}$–$C_{22}$) amine oxide emulsion stabilizer in an amount of about 0.1% to about 5% based on the weight of the composition.

4. The composition of claim 1 having a pH of about 4.5 to about 7.5.

5. The composition of claim 1, wherein the composition includes a viscosity increasing agent in an amount of about 0.1% to about 10% by weight of the composition capable of raising the viscosity of the composition to at least about 3,000 centipoises.

6. The composition of claim 1 further including a zwitterionic detergent in an amount of about 5% to about 15% by weight of the composition.

7. The composition of claim 1, wherein the composition includes a betaine surfactant in an amount of about 5% to about 25% by weight of the composition.

8. The composition of claim 7, wherein the betaine surfactant is cocamidopropyl hydroxysultaine.

9. The composition of claim 7, wherein the betaine surfactant is cocoampho-carboxyglycinate.

10. The composition of claim 7, wherein the betaine surfactant is lauroampho-carboxyglycinate.

11. The composition of claim 2, wherein the surfactant is laureth-5-carboxylic acid.

12. The composition of claim 1, wherein the composition includes less than about 9% by weight of the composition of an anionic surfactant selected from the group consisting of a long chain ($C_{12-22}$) alkyl sulfate; a long chain ($C_{12-22}$) alkyl ether sulfate; and a long chain ($C_{12-22}$) alkyl sulfonate.

13. A method of cleansing and conditioning hair, simultaneously, while maintaining a high foam level and excellent cleansing in a mild shampoo composition comprising contacting the hair with a mild conditioning shampoo composition comprising water, an anionic surfactant in an amount of about 5% to about 25% by weight of the composition, and a cationic oil-soluble, water-dispersible cross-linked quaternary acrylate/acrylamide copolymer in an amount of about 0.1% to about 20% by weight of the composition.

14. The method of claim 13, wherein the anionic surfactant is a low irritation surfactant selected from the group consisting of disodium laureth sulfosuccinate; disodium lauroamido MEA sulfosuccinate; disodium ricinoleamido MEA sulfosuccinate; ceteareth-25-carboxylic acid; trideceth-7-carboxylic acid; pareth-25-6-carboxylic acid; trideceth-4-carboxylic acid; trideceth-19-carboxylic acid; sodium trideceth-12-carboxylate; sodium ceteth-13-carboxylate; laureth-5-carboxylic acid; sodium laureth-13-carboxylate; sodium oleth-13-carboxylate; sodium ceteareth-5-carboxylate; sodium ceteareth-9-carboxylate; isosteareth-6-carboxylic acid; and isosteareth-11-carboxylic acid.

15. The method of claim 13, wherein the conditioning shampoo further includes an amine oxide emulsion stabilizer having a long chain ($C_{12-22}$) alkyl substituent in an amount of about 0.1% to about 5% based on the weight of the composition.

16. The method of claim 13, wherein the conditioning shampoo further includes a viscosity increasing agent in an amount of about 0.1% to about 10% by weight of the composition capable of raising the viscosity of the composition to at least about 3,000 centipoises.

17. The method of claim 13, wherein the composition includes a zwitterionic detergent in an amount of about 5% to about 15% by weight of the composition.

18. The method of claim 13, wherein the composition includes a betaine surfactant in an amount of about 5% to about 25% by weight of the composition.

19. The method of claim 18, wherein the betaine surfactant is cocamidopropyl hydroxysultaine.

20. The method of claim 18, wherein the betaine surfactant is cocoampho-carboxyglycinate.

21. The method of claim 18, wherein the betaine surfactant is lauroampho-carboxyglycinate.

22. The method of claim 14, wherein the carboxylate surfactant is laureth-5-carboxylic acid.

* * * * *

UNITED STATES PATENT AND TRADEMARK OFFICE
CERTIFICATE OF CORRECTION

PATENT NO. : 5,221,530
DATED : JUNE 22, 1993
INVENTORS : BEN JANCHITRAPONVEJ, ET AL.

It is certified that error appears in the above-identified patent and that said Letters Patent is hereby corrected as shown below:

Column 5, line 27, after "Many" delete "addition" and substitute therefor -- additional --; and Column 6, line 28, after "Laureth-5-Carboxylic Acid (SANDOPAN® LA 8)" insert as a new line -- Sodium Laureth-13-Carboxylate --.

Signed and Sealed this

Twenty-sixth Day of July, 1994

*Attest:*

BRUCE LEHMAN

*Attesting Officer*     *Commissioner of Patents and Trademarks*